United States Patent
Schirmer et al.

(10) Patent No.: US 7,166,740 B2
(45) Date of Patent: Jan. 23, 2007

(54) PROCESS FOR THE PRODUCTION OF TRIIODOTRIMESIC ACID

(75) Inventors: Heiko Schirmer, Berlin (DE); Ulrich Niedballa, Berlin (DE); Hannelore Niedballa, Berlin (DE); Johannes Platzek, Berlin (DE); Jose Luis Martin, Madrid (ES); Juan R. Harto, Madrid (ES); Jose Carretero, Madrid (ES)

(73) Assignee: Schering AG, Berlin (DE)

( * ) Notice: Subject to any disclaimer, the term of this patent is extended or adjusted under 35 U.S.C. 154(b) by 283 days.

(21) Appl. No.: 10/890,521

(22) Filed: Jul. 14, 2004

(65) Prior Publication Data

US 2005/0113598 A1 May 26, 2005

Related U.S. Application Data

(60) Provisional application No. 60/487,976, filed on Jul. 18, 2003.

(30) Foreign Application Priority Data

Jul. 14, 2003 (DE) .............................. 103 32 552.2

(51) Int. Cl.
*C07C 69/00* (2006.01)
*C07C 51/255* (2006.01)

(52) U.S. Cl. ...................................... 560/130; 562/409
(58) Field of Classification Search ................ 560/130; 562/409

See application file for complete search history.

(56) References Cited

U.S. PATENT DOCUMENTS

| 4,269,819 A | 5/1981 | Gries |
| 5,047,228 A | 9/1991 | Gries et al. |
| 5,882,628 A | 3/1999 | Almen et al. |

FOREIGN PATENT DOCUMENTS

| DE | 1271702 | 7/1968 |
| DE | 2831496 | 1/1980 |
| DE | 3001292 | 7/1981 |
| EP | 0032387 | 7/1981 |

OTHER PUBLICATIONS

Database Compendex Engineering Information, Inc., New York, NY, US: Molchanova V V et al: okislenie polimetilbenzolov permanganatom kaliya: XP002305146 Database accession No. EiX81050004547 Zusammenfassung & KHIM PROM. Nr. 10, 1980, Seiten 588-589, Oxidation Of Polymethylbenzenes With Ptoassium Permanganate V.V. Molchanova, L.,. Gus'kova, I. P. Kolenko, The Soviet Chemical Industry, 12:10 (1980), and CAS Abstract 94139399 CA: 94(17) 139399w Journal Oxidation Of Polymethylbenzenes By Potassium Permanganate Author(s): Molchanova. V.V., Gus'kova, L.M.; Kolenko. I.P. Location USSR Journal: Khim. Prom-st. (Moscow) Date 1980 No. 10 pp. 588-589.

*Primary Examiner*—Taylor Victor Oh

(74) *Attorney, Agent, or Firm*—Millen, White, Zelano & Branigan, P.C.

(57) ABSTRACT

A new process for the production of triiodotrimesic acid that is used as an intermediate product for the synthesis of x-ray contrast media is described.

8 Claims, No Drawings

PROCESS FOR THE PRODUCTION OF TRIIODOTRIMESIC ACID

This application claims the benefit of the filing date of U.S. Provisional Application Ser. No. 60/487,976 filed Jul. 18, 2003, which is incorporated by reference herein.

Triiodotrimesic acid (formula I) is an important intermediate product for the production of nonionic triiodized x-ray contrast media. Thus, the production of tris-amides of triiodotrimesic acid is described in, for example, DE 3001292 (Schering). Such compounds are especially advantageous because of their favorable pharmacological properties. Attempts to make economic use of these tris-amides have failed because, up until now, no commercially usable way has been found to access the actual starting compound, the triiodotrimesic acid. Further development of a contrast medium with especially good properties, iosimide, which was already in phase III of the clinical examinations, was unsuccessful due to the high production costs of the triiodotrimesic acid.

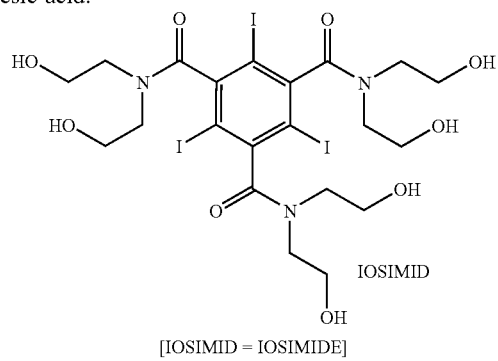

[IOSIMID = IOSIMIDE]

Thus, in DE 2831496, the production of the triiodotrimesic acid, starting from nitroisophthalic acid, is described:

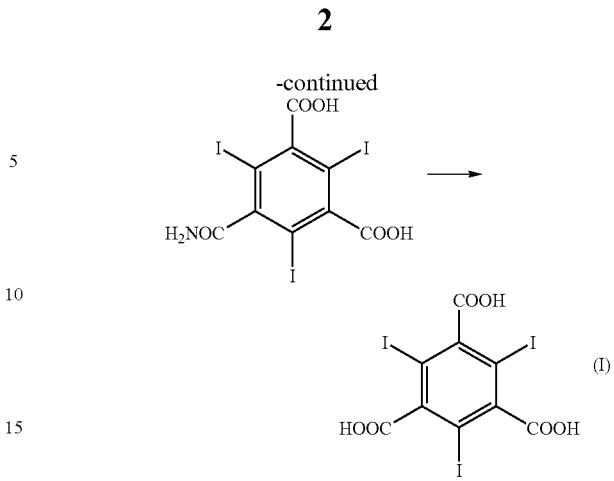

In this process, nitroisophthalic acid is hydrogenated to form an amino compound and then iodized with chloroiodine. The introduction of the missing carboxyl group can be accomplished with a Sandmeyer reaction ($HNO_2$/KCN/CuCN). This reaction step proved very critical especially in increasing coarseness of the batch, since, on the one hand, hydrogen cyanide is produced, and in addition the copper ions must be used in excess. The removal of copper wastes from the reaction water can be considered especially critical on an industrial scale. A critical step is also the complete saponification of nitrile to carboxylic acid. In this connection, the process has to pass through an intermediate stage, the amide, which proved very difficult to hydrolyze.

In another patent (NYCOMED: U.S. Pat. No. 5,882,628), intermediate stages are described that were considered as starting products for the synthesis of triiodotrimesic acid:

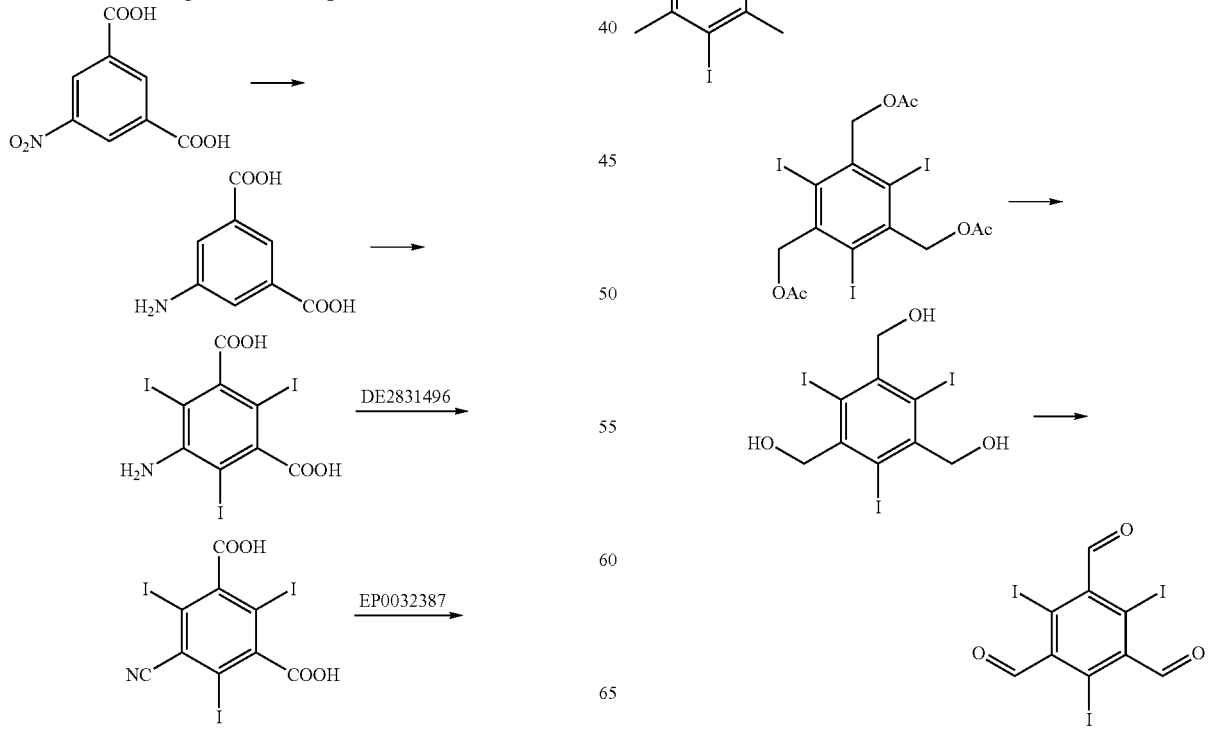

Triiodomesitylene is converted under acetylating conditions in an oxidation reaction with potassium permanganate/acetic anhydride/acetic acid/sulfuric acid into triacetate (yield: 35%). The triacetate is isolated and saponified with potassium carbonate in methanol to tris alcohol (yield: 94%). The tris alcohol is then reacted to form tris aldehyde by Swern oxidation in dimethyl sulfoxide as a solvent in a yield of 67%.

Additional oxidation to tricarboxylic acid was not described in this patent and also is not reported with this step in literature.

There was therefore the need for a new synthesis that provides triiodotrimesic acid in a higher total yield from advantageous environmental and safety standpoints and that also has the capacity for increasing coarseness of the batch. These requirements are, surprisingly enough, met by the new two-stage synthesis that is present here. The following synthesis diagram shows the new method of synthesis that starts from triiodomesitylene:

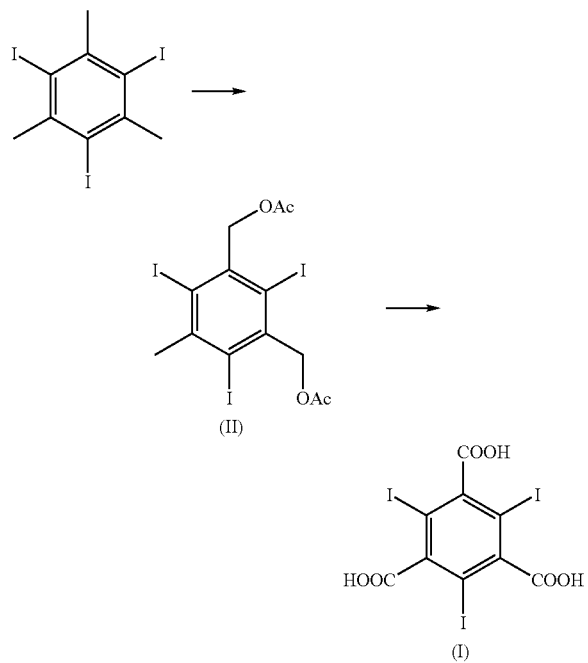

In this connection, starting from triiodomesitylene, the reaction is performed with potassium or sodium permanganate in a mixture that consists of acetic acid anhydride, acetic acid and sulfuric acid in a volume ratio of 15–30: 10–20: 1.25–3.5, preferably 20:15:2.5. The sulfuric acid is used at the concentration of 70%–100%, preferably 95–100%. The reaction is carried out at temperatures of 10 to 120° C., preferably 20–100° C., especially preferably 40–80° C. The reaction period is 12–36 hours, preferably 15–25 hours.

Then, it is distilled off. This can be carried out directly from the batch, whereby the pressure optionally is reduced. In this case, a mixture that consists of acetic acid and acetic anhydride is obtained. Also, however, only water can be added to destroy excess acetic acid anhydride, and then pure acetic acid is distilled off. The recovered acetic acid can be reused.

Then, the sulfuric acid is neutralized in the residue by adding an inorganic base such as sodium hydroxide solution, potassium hydroxide solution, or calcium hydroxide in solid form, or, preferably, as an aqueous solution, and the concentration by evaporation is continued.

After concentration by evaporation is completed, water is added at temperatures of between 60–100° C., then it is absorptively precipitated, and the precipitated 1,3,5-triiodo-2,4-diacetoxymethylene-6-methylbenzene (II) is filtered off, which is washed with water and methanol and then dried.

In the next reaction step, the 1,3,5-triiodo-2,4-diacetoxymethylene-6-methylbenzene (II) is introduced into water at temperatures of 60–100° C., preferably 80–100° C. (reflux) and mixed with an aqueous solution of an inorganic base, preferably sodium hydroxide solution, potassium hydroxide solution, calcium hydroxide, sodium carbonate or potassium carbonate, but especially preferably NaOH or KOH. The period of dropwise addition of the base is 30 minutes to 10 hours, preferably 30 minutes to 3 hours. Then, it is stirred for 1 to 24 hours, preferably 3–12 hours, especially preferably 4–8 hours, at temperatures of between 60 and 100° C., especially preferably 80–100° C. Then, it is neutralized with an inorganic acid (pH=6–7), preferably hydrochloric acid, hydrobromic acid or sulfuric acid, but especially preferably concentrated hydrochloric acid; magnesium sulfate is added to the hot reaction solution, and an aqueous potassium or sodium permanganate solution is added in drops and then stirred for 1 to 24 hours, preferably 1–12 hours, especially preferably 2–4 hours at temperatures of between 60 and 100° C., especially preferably 80–100° C.

The subsequent working-up can be carried out in different ways:

1. Excess oxidizing agent can be destroyed by adding a reducing agent in solid or dissolved form (aqueous solution). For this purpose, in particular inorganic sulfites or hydrogen sulfites, such as sodium sulfite/hydrogen sulfite or potassium sulfite/hydrogen sulfite, especially preferably sodium sulfite or lower alcohols such as methanol, ethanol, isopropanol, and glycol are suitable. The latter takes place at temperatures of between 10 to 100° C., preferably 20–80° C. Then, a pH of 0.1–3, preferably 0.5–1, is set by adding sulfuric acid, and the product is extracted by extraction with an organic solvent, such as ethyl acetate, propyl acetate, methyl-butyl ether (MTB), tetrahydrofuran (THF), n-butanol, methyl-THF, dichloromethane, or toluene. Ethyl acetate and MTB are preferred. The organic phases can optionally be washed with water, brine or acidified water and are evaporated to the dry state. It has proven especially advantageous to redistill directly the solvent that is used for crystallization. In this case, the first solvent is replaced by the second solvent during the distillation by continuous addition of a second solvent. As a solvent for crystallization, especially cyclohexane and n-heptane, as well as their mixtures with ethyl acetate, toluene and MTB, have proven their value.

In many cases, an extraction with an organic solvent, as described above, can also be eliminated. To this end, it is largely evaporated to the dry state under reduced pressure, and then water is largely removed by adding an azeotrope-forming solvent such as methanol, ethanol, isopropanol, dichloromethane, MTB, ethyl acetate, butyl acetate, butanol, toluene or THF. The amount of residual water is determined by Karl-Fischer (KF) titration. Then, the remaining residue is absorptively precipitated with an organic solvent, such as methanol, ethanol, isopropanol, dichloromethane, MTB, ethyl acetate, butyl acetate, butanol, toluene or THF at temperatures of between 20–100° C., and salts are filtered out. The filtrate can be evaporated to the dry state or else, as described above, a solvent that is suitable for crystallization can be redistilled.

2. In many cases, it has proven advantageous not to add any reducing agent but rather to set the pH to 0.1–3, but preferably 0.1–1, by adding sulfuric acid and then to evaporate it to the dry state as described above under reduced pressure and to absorptively precipitate the residue with an organic solvent (analogous procedure to that under 1).

The synthesis process that is described here is characterized by several important advantages compared to the process of the prior art:

The inexpensive and nontoxic potassium or sodium permanganate is used as the only oxidizing agent. The manganese wastes that are produced can be made reusable in a recycling process by further oxidation.

The process is robust and can easily be implemented on a multi-ton scale. It is distinguished by an environmentally sound solvent. The process is inexpensive in implementation, consists of only two stages and provides a high total yield of 80–85% of theory.

This process thus represents a valuable contribution to the production of an intermediate stage of the triiodized trisamides that are important for medical diagnosis.

The examples below are used to describe the new process:

Production of Triiodotrimesitylene

Carried out according to Synthesis 6, 486 (1980); WO 96/09282, J. Med. Chem. (2000) 43 (10), 1940 or according to Synlett (2002), (4), 598

Production of 1,3,5-Triiodo-2,4-diacetoxymethylene-6-methylbenzene (II)

400 g (803 mmol) of triiodomesitylene is suspended in 0.9 l of acetic anhydride, 1.4 l of acetic acid and 121 ml of concentrated sulfuric acid, and 160 g (1.01 mol) of potassium permanganate is added in portions (over 2 hours) at 40° C. and stirred for 18 hours at 40° C. After the reaction is completed, 152 ml of water is carefully added while being stirred, and stirring is continued for 2 hours at room temperature. Then, 363.2 ml of 50% sodium hydroxide solution (exactly the amount to neutralize the sulfuric acid!) is added. Then, it is largely distilled off (concentrated by evaporation) under reduced pressure. 4 l of water is added in drops while being stirred, and it is then stirred for one hour at 10° C. The deposited precipitate is suctioned off, rewashed twice with 1.5 l of water each and with 500 ml of methanol, and it is dried in a vacuum at 50° C.

Yield: 0.456 kg (93% of theory)
Elementary analysis:

| Cld.: | C 24.43 | H 2.13 | J 62.01 |
|---|---|---|---|
| Fnd.: | C 24.26 | H 2.09 | J 62.31 |

Production of Triiodotrimesic Acid (I) (Variant A)

250 g (407 mmol) of 1,3,5-triiodo-2,4-diacetoxymethylene-6-methylbenzene is suspended in 2.5 l of water and mixed carefully at 90° C. with 200 ml of 50% sodium hydroxide solution and stirred for 5 hours at 90° C. Then, it is neutralized with concentrated hydrochloric acid (pH=6–7), mixed with 367 g (1.488 mol) of magnesium sulfate, a solution that consists of 411 g (2.604 mol) of potassium permanganate in 4 l of water is added in drops, and it is stirred for 2 hours under reflux. It is cooled to room temperature (RT), 50 g of sodium sulfite is added, and it is stirred for one hour at room temperature. Then, it is set at a pH of 1 with 50% sulfuric acid. 2 l of ethyl acetate is added, and it is thoroughly stirred. The organic phase is separated, and the aqueous phase is subsequently re-extracted 2× with 0.5 l of ethyl acetate. The organic phases are combined, rewashed once with 2.5 l of water and then redistilled with cyclohexane. During cooling (0° C.), the product crystallizes out.

Yield: 206 g (86% of theory)
Elementary analysis:

| Cld.: | C 18.39 | H 0.51 | J 64.77 |
|---|---|---|---|
| Fnd.: | C 18.47 | H 0.56 | J 64.65 |

Production of Triiodotrimesic Acid (I) (Variant B)

250 g (407 mmol) of 1,3,5-triiodo-2,4-diacetoxymethylene-6-methylbenzene is suspended in 2.5 l of water and mixed carefully at 90° C. with 200 ml of 50% sodium hydroxide solution and stirred for 5 hours at 90° C. Then, it is neutralized with concentrated hydrochloric acid (pH=6–7), mixed with 367 g (1.488 mol) of magnesium sulfate, a solution that consists of 411 g (2.604 mol) of potassium permanganate in 4 l of water is added in drops, and it is stirred for 2 hours under reflux. It is cooled to room temperature (RT), 50 g of sodium sulfite is added, and it is stirred for one hour at room temperature. Then, it is set at a pH of 1 with 50% sulfuric acid. 2 l of ethyl acetate is added, and it is thoroughly stirred. The organic phase is separated, and the aqueous phase is subsequently re-extracted 2× with 0.5 l of ethyl acetate. The organic phases are combined and rewashed once with 2.5 l of water. The ethyl acetate solution is distilled off to remove water azeotropically (water content according to Karl-Fischer titration <0.2%). A thus produced solution can be used for further reaction (e.g., production of acid chloride with $SOCl_2$). By concentration by evaporation of an aliquot, the yield was determined.

Yield: 211 g (88% of theory)
Elementary analysis:

| Cld.: | C 18.39 | H 0.51 | J 64.77 |
|---|---|---|---|
| Fnd.: | C 18.50 | H 0.62 | J 64.54 |

Production of Triiodotrimesic Acid (I) (Variant C)

250 g (407 mmol) of 1,3,5-triiodo-2,4-diacetoxymethylene-6-methylbenzene is suspended in 2.5 l of water and mixed carefully at 90° C. with 200 ml of 50% sodium hydroxide solution, and it is stirred for 5 hours at 90° C. Then, it is neutralized with concentrated hydrochloric acid (pH=6–7), mixed with 367 g (1.488 mol) of magnesium sulfate, a solution that consists of 411 g (2.604 mol) of potassium permanganate in 4 l of water is added in drops, and it is stirred for 2 hours under reflux. It is cooled to room temperature (RT), 50 g of sodium sulfite is added, and it is stirred for one hour at room temperature. Then, it is set at a pH of 1 with 50% sulfuric acid. It is largely concentrated by evaporation in a vacuum, and residual water is distilled off azeotropically by adding isopropanol. The isopropanol is continuously added. At a water content <1% (KF titration), another 10 l of isopropanol is added, and it is stirred for one hour at 40° C. Filtration is done from salt paste, and it is flushed two more times with 3 l of isopropanol. The filtrate is evaporated to the dry state in a vacuum.

Yield: 213 g (89% of theory)
Elementary analysis:

| Cld.: | C 18.39 | H 0.51 | J 64.77 |
|---|---|---|---|
| Fnd.: | C 18.46 | H 0.59 | J 64.64 |

Production of Triiodotrimesic Acid (I) (Variant D)

250 g (407 mmol) of 1,3,5-triiodo-2,4-diacetoxymethylene-6-methylbenzene is suspended in 2.5 l of water and mixed carefully at 90° C. with 200 ml of 50% sodium hydroxide solution and stirred for 5 hours at 90° C. Then, it is neutralized with concentrated hydrochloric acid (pH=6–7), mixed with 367 g (1.488 mol) of magnesium sulfate, a solution that consists of 411 g (2.604 mol) of potassium permanganate in 4 l of water is added in drops, and it is stirred for 2 hours under reflux. It is cooled to room temperature (RT), 50 g of sodium sulfite is added, and it is stirred for one hour at room temperature. Then, it is set at a pH of 1 with 50% sulfuric acid. It is largely concentrated by evaporation in a vacuum, and residual water is azeotropically distilled out by adding ethanol (continuous addition of ethanol). At a water content <1% (KF), another 10 l of ethanol is added, and it is stirred for one hour at 40° C. Filtration is done from salt paste, and it is flushed two more times with 5 l of isopropanol. The filtrate is evaporated to the dry state in a vacuum.

Yield: 215 g (90% of theory)
Elementary analysis:

| Cld.: | C 18.39 | H 0.51 | J 64.77 |
|---|---|---|---|
| Fnd.: | C 18.41 | H 0.54 | J 64.59 |

Production of Triiodotrimesic Acid (I) (Variant E)

250 g (407 mmol) of 1,3,5-triiodo-2,4-diacetoxymethylene-6-methylbenzene is suspended in 2.5 l of water and mixed carefully at 90° C. with 200 ml of 50% sodium hydroxide solution, and it is stirred for 5 hours at 90° C. Then, it is neutralized with concentrated hydrochloric acid (pH=6–7), mixed with 367 g (1.488 mol) of magnesium sulfate, a solution that consists of 411 g (2.604 mol) of potassium permanganate in 4 l of water is added in drops, and it is stirred for 2 hours under reflux. It is cooled to room temperature (RT), 50 g of sodium sulfite is added, and it is stirred for one hour at room temperature. Then, it is set at a pH of 1 with 50% sulfuric acid. It is largely concentrated by evaporation in a vacuum, and residual water is azeotropically distilled out by adding isopropanol (continuous addition of isopropanol). At a water content <1% (KF), another 10 l of isopropanol is added, and it is stirred for one hour at 40° C. Filtration is done from salt paste, and it is flushed two more times with 5 l of isopropanol. The filtrate is evaporated to the dry state in a vacuum.

Yield: 214 g (90% of theory)
Elementary analysis:

| Cld.: | C 18.39 | H 0.51 | J 64.77 |
|---|---|---|---|
| Fnd.: | C 18.47 | H 0.55 | J 64.71 |

Production of Triiodotrimesic Acid (I) (Variant F)

250 g (407 mmol) of 1,3,5-triiodo-2,4-diacetoxymethylene-6-methylbenzene is suspended in 2.5 l of water and mixed carefully at 90° C. with 200 ml of 50% sodium hydroxide solution, and it is stirred for 5 hours at 90° C. Then, it is neutralized with concentrated hydrochloric acid (pH=6–7), mixed with 367 g (1.488 mol) of magnesium sulfate, a solution that consists of 411 g (2.604 mol) of potassium permanganate in 4 l of water is added in drops, and it is stirred for 2 hours under reflux. It is cooled to room temperature (RT), 50 g of sodium sulfite is added, and it is stirred for one hour at room temperature. Then, it is set at a pH of 1 with 50% sulfuric acid. It is largely concentrated by evaporation in a vacuum, and residual water is azeotropically distilled off by adding ethanol (continuous addition of ethanol). At a water content <1% (KF), another 10 l of ethanol is added, and it is stirred for one hour at 40° C. Filtration is done from salt paste, and it is flushed two more times with 5 l of ethanol. The filtrate is evaporated to the dry state in a vacuum.

Yield: 213 g (89% of theory)
Elementary analysis:

| Cld.: | C 18.39 | H 0.51 | J 64.77 |
|---|---|---|---|
| Fnd.: | C 18.44 | H 0.54 | J 64.66 |

Production of Triiodotrimesic Acid (I) (Variant G)

250 g (407 mmol) of 1,3,5-triiodo-2,4-diacetoxymethylene-6-methylbenzene is suspended in 2.5 l of water and mixed carefully at 90° C. with 200 ml of 50% sodium hydroxide solution, and it is stirred for 5 hours at 90° C. Then, it is neutralized with concentrated hydrochloric acid (pH=6–7), mixed with 367 g (1.488 mol) of magnesium sulfate, a solution that consists of 411 g (2.604 mol) of potassium permanganate in 4 l of water is added in drops, and it is stirred for 2 hours under reflux. It is cooled to room temperature (RT), 50 g of sodium sulfite is added, and it is stirred for one hour at room temperature. Then, it is set at a pH of 1 with 50% sulfuric acid. It is largely concentrated by evaporation in a vacuum, and residual water is azeotropically distilled out by adding methanol (continuous addition of methanol). At a water content <2% (KF-titration), another 10 l of methanol is added, and it is stirred for one hour at 40° C. Filtration is done from salt paste, and it is flushed two more times with 5 l of methanol. The filtrate is evaporated to the dry state in a vacuum.

Yield: 213 g (89% of theory)
Elementary analysis:

| Cld.: | C 18.39 | H 0.51 | J 64.77 |
|---|---|---|---|
| Fnd.: | C 18.36 | H 0.62 | J 64.72 |

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius, and all parts and percentages are by weight, unless otherwise indicated.

The entire disclosure[s] of all applications, patents and publications, cited herein and of corresponding German Application No. 103 32 552.2, filed Jul. 14, 2003, and U.S. Provisional Application Ser. No. 60/487,976, filed Jul. 18, 2003, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for preparing triiodotrimesic acid comprising reacting triiodomesitylene in an oxidation process with potassium or sodium permanganate in a mixture that consists of acetic acid anhydride, acetic acid and sulfuric acid at a temperature of 10 to 120° C. for 12 to 36 hours, and then isolating the obtained 1,3,5-triiodo-2,4-diacetoxymethylene-6-methylbenzene which is then treated with a base for 1.5 to 34 hours at a temperature of 60 to 100° C., then the reaction solution is neutralized and then it is treated with an aqueous potassium or sodium permanganate solution at a temperature of 60 to 100° C. for 1 to 24 hours in an oxidation process.

2. A process according to claim 1, wherein the reaction that forms 1,3,5—triiodo—2,4—diacetoxymethylene—6—methylbenzene is performed at 40 to 80° C.

3. A process according to claim 1, wherein the reaction that forms 1,3,5—triiodo—2,4—diacetoxymethylene—6—methylbenzene is performed for 15 to 25 hours.

4. A process according to claim 1, wherein the basic treatment of the intermediate product is performed at 80 to 100° C.

5. A process according to claim 1, wherein the basic treatment of 1,3,5—triiodo—2,4—diacetoxymethylene—6—methylbenzene is performed for 3 to 12 hours.

6. A process according to claim 1, wherein the oxidation of 1,3,5—triiodo—2,4—diacetoxymethylene—6—methylbenzene is performed at 80 to 100° C.

7. A process according to claim 1, wherein the oxidation of 1,3,5—triiodo—2,4—diacetoxymethylene—6—methylbenzene is performed for 2 to 4 hours.

8. 1,3,5-Triiodo-2,4-diacetoxymethylene-6-methylbenzene.

* * * * *